United States Patent
Castellini

(10) Patent No.: US 6,533,735 B2
(45) Date of Patent: Mar. 18, 2003

(54) DEVICE FOR DETECTING INFECTIOUS AGENTS

(75) Inventor: Franco Castellini, Bologna (IT)

(73) Assignee: Castellini, S.p.A., Bologna (IT)

( * ) Notice: Subject to any disclaimer, the term of this patent is extended or adjusted under 35 U.S.C. 154(b) by 0 days.

(21) Appl. No.: 09/886,603

(22) Filed: Jun. 21, 2001

(65) Prior Publication Data

US 2002/0001838 A1 Jan. 3, 2002

(30) Foreign Application Priority Data

Jun. 30, 2000 (IT) ........................................ BO20A0388

(51) Int. Cl.[7] .................................................. A61B 5/00
(52) U.S. Cl. ..................................................... 600/584
(58) Field of Search ................................ 600/573, 581, 600/584; 604/317–319, 403, 404, 416; 422/102

(56) References Cited

U.S. PATENT DOCUMENTS 3,727,603 A * 4/1973 Holbrook ................... 600/584
6,171,280 B1 * 1/2001 Imazu et al. ................ 604/118
6,372,182 B1 * 4/2002 Mauro et al. ................ 422/56

FOREIGN PATENT DOCUMENTS

EP 0990900 A2 4/2000

\* cited by examiner

Primary Examiner—Max F. Hindenburg
(74) Attorney, Agent, or Firm—Fay, Sharpe, Fagan, Minnich & McKee, LLP

(57) ABSTRACT

A device for detecting infectious agents, antibodies or other biological indicators in a biological fluid drawn from a patient comprises the following: a first endpiece for collecting a sample of a fluid from a patient and mixing a predetermined quantity of said fluid with means for reacting with and/or conditioning the biological agents; a suction tube forming an extension of the first endpiece and designed to completely mix the fluid with the reagent and/or conditioning means and to introduce the mixture in a sealed container that receives the mixture consisting of the fluid and the reagent and/or conditioning means; and means for opening the container designed to enable a controlled discharge of the mixture into corresponding detecting means for displaying a result.

17 Claims, 2 Drawing Sheets

DEVICE FOR DETECTING INFECTIOUS AGENTS

BACKGROUND OF THE INVENTION

The present invention relates to a device for detecting infectious agents, antibodies or other biological indicators in a biological fluid from a patient undergoing treatment, especially in a medical or dental surgery, on or with a dental unit.

The invention addresses dental surgeries in particular. In dental surgeries, dental units of the latest generation are of extremely high quality in terms of functionality, appliance control and, above all, level of sterility. This high quality is the result of constant research and development of solutions for the improvement of dental units which, in the philosophy of the Applicant, means being able to offer health-care providers and patients an effective means of controlling the risk of cross-infection.

Indeed, increased awareness of the risk of cross-infection has led manufacturers of dental equipment to develop more and more solutions capable of allowing treatment to be carried out under conditions of maximum safety for both health-care providers and patients. It is in this perspective that we must view the development of recent devices for disinfecting/sterilizing dental handpieces and dental unit water and air lines (even between successive patient treatments) and the use of disposable instruments.

There is, however, still much concern about certain diseases such as hepatitis C (HCV), which, as all health-care providers now agree, can also be transmitted during dental treatment.

To ascertain the presence of infectious agents in the medical instruments to be used on patients undergoing treatment (thus guaranteeing the safety of both patients and health-care providers), the Applicant has designed and developed a method and device, disclosed in European patent application EP-990.900, where a fluid sample from the patient is drawn by the aspirator on the dental unit, mixed with a reagent and the result of the reaction displayed on the device itself.

On the basis of this method, the Applicant has aimed to improve on this device in order to develop a kit capable of immediately detecting any of a wide range of biological agents directly in the dental surgery using the blood present in the oral cavity of a patient during a dental treatment such as cleaning or other routine operation within the oral cavity.

SUMMARY OF THE INVENTION

Accordingly, the present invention provides a device for detecting infectious agents, antibodies or other biological indicators in a biological fluid drawn from a patient undergoing a treatment in a dental surgery, said device comprising the following: a first endpiece for collecting a sample of a fluid from a patient and mixing a predetermined quantity of it with means for reacting with and/or conditioning the biological agents; a suction tube forming an extension of the first endpiece and designed to thoroughly mix the fluid with the reagent and/or conditioning means and to introduce the mixture in a sealed container that receives the mixture consisting of the fluid and the reagent and/or conditioning means; and means for opening the container designed to permit a controlled discharge of the mixture into corresponding detecting means for displaying the result.

BRIEF DESCRIPTION OF THE DRAWINGS

The technical features of the present invention, in accordance with the above-mentioned aims, are set out in the claims below and the advantages more clearly illustrated in the detailed description which follows, with reference to the accompanying drawings, which illustrate a preferred embodiment of the invention without restricting the scope of the inventive concept, and in which:

DESCRIPTION OF THE PREFERRED EMBODIMENTS

Figure 1:
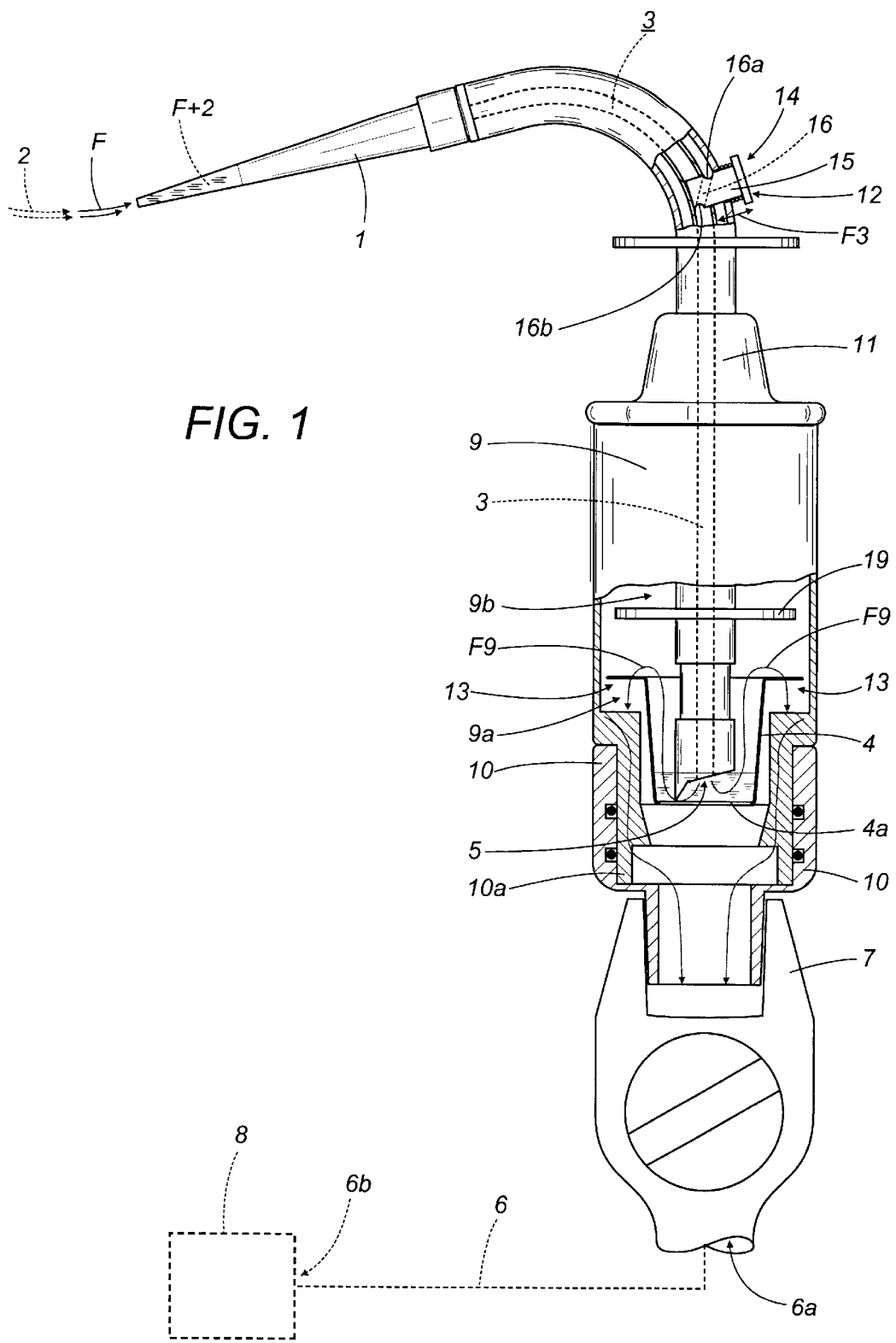
FIG. 1 is a side view, with some parts cut away and others in cross section, of a device for detecting infectious agents according to the present invention shown in a first fluid collecting configuration.
Figure 2:
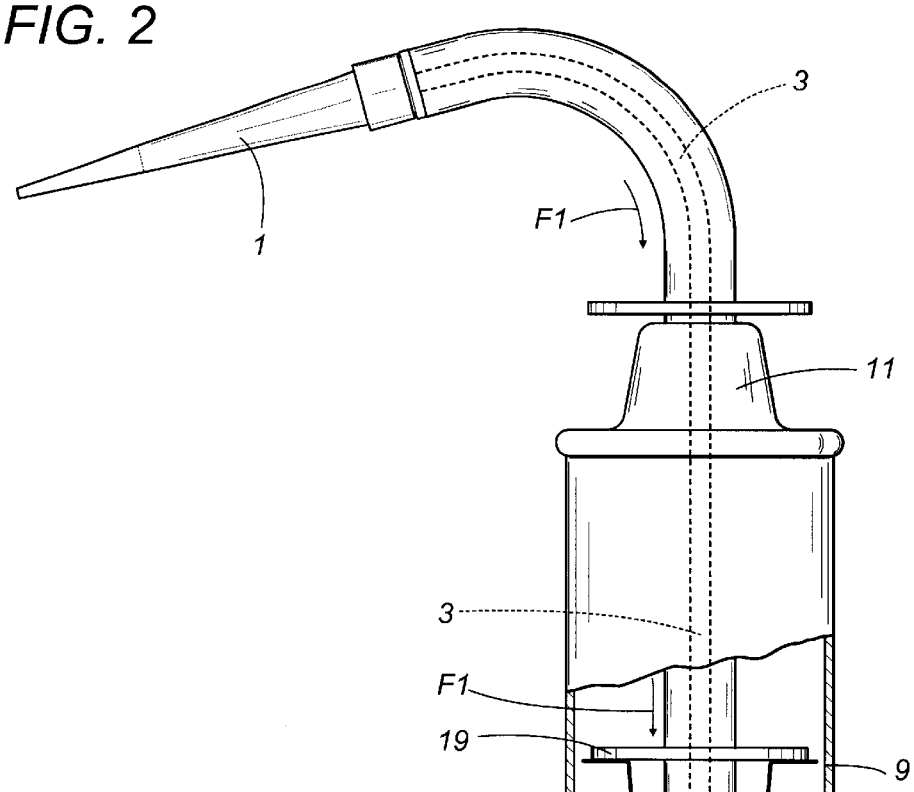
FIG. 2 is a side view, with some parts cut away and others in cross section, of the device illustrated in FIG. 1 shown in a discharging configuration.

With reference to the accompanying drawings, in particular FIGS. 1 and 2, the device disclosed is used to detect infectious agents, antibodies or other biological indicators in a biological fluid drawn from a patient undergoing a treatment, in particular in a dental surgery.

This device comprises a first endpiece 1 for collecting a sample of a fluid F (indicated by a series of arrows) from a patient and mixing a predetermined quantity of said fluid with means 2 which are designed to react with and/or condition the biological agents and which differ according to the type of biological agents to be detected.

A suction tube 3 forming an extension of the first endpiece 1 allows the fluid F to be thoroughly mixed with reagent and/or conditioning means 2 and the mixture F+2 to be introduced in a container 4 designed to receive the mixture F+2 itself.

The device further comprises means 5 for opening the container 4 in such a way as to permit a controlled discharge of the mixture F+2 into corresponding detecting means 20 designed to analyze the mixture and display the result of the reaction.

As shown in FIG. 1 and as stated above, the device can be used in a dental surgery furnished with a dental unit having at least one suction conduit 6 extending from an outer operative end 6a, which has a second endpiece 7 that is designed to accommodate a suction cannula, to an end 6b that leads into a tank or drain 8 (of conventional type and therefore illustrated schematically) forming part of the dental unit.

The embodiment illustrated is designed to be used in combination with the suction equipment of the dental unit but this must not be construed as restricting the scope of the invention which may also be used with a separate suction appliance independent of the dental unit.

Looking more closely at the constructional details, the tube 3 and the container 4 are housed in a casing 9 equipped with means 10 for connecting the operative end 6a of the conduit 6 in such a way that the conduit can be used to suck in and mix the fluid F and the reagent 2.

The casing 9 comprises a hollow, cylindrical body equipped at one end with a cylindrical fitting 10a, that can be connected to the connecting means 10 which can be detachably fitted to the operative end 6a of the suction conduit 6, and at the other end with an element 11 for supporting the suction tube 3 protruding from the casing 9.

The suction tube 3 is fitted directly with the aforementioned opening means 5. The means 5 for opening the container 4 comprise a sharp taper at one end of the tube 3, located inside the container 4 itself, designed to tear the bottom 4a of the container 4 when the tube 3 is moved axially, thus allowing the mixture F+2 to be discharged (see FIG. 2 and arrows F1).

The tube 3 is also equipped with limit stop means 19 designed to allow the bottom 4a of the container 4 to be torn completely and to keep the tube 3 in a position in which the mixture F+2 can flow out. The limit stop means 19 may consist of a disc 19 connected to the tube 3 at a point close to the top of the container 4: thus, the axial movement of the tube 3 when the bottom 4a of the container 4 is completely torn but before the tube can go through the bottom of the casing 9 so that it does not touch the detecting means 20.

The tube 3 may further comprise manual control means 12 for turning on the suction so that the fluid F and the reagent 2 are sucked into the first endpiece 1 separately and in a controlled manner. The suction generated by the conduit 6 is conveyed and used by the tube 3 through an opening 13 in the casing 9 which allows a lower chamber 9a of the casing 9 to communicate with an upper chamber 9b and through which the suction can also act on the tube 3 inside the container 4 (see arrows F9 in FIG. 1).

The manual control means 12 for turning on the controlled suction of the fluid F and reagent 2 consist of a pushbutton 14 connected to, and able to slide radially through, the tube 3 and equipped with a body 15 with a conduit 16 running transversally through the body 15 itself.

The conduit 16 has two openings 16a and 16b, which are axially offset relative to each other so as to enable the fluid F and the reagent 2 to be sucked into the first endpiece 1 when the body 15 is completely inside the tube 3, and to enable the fluid F to be visible at the free end of the first endpiece 1 when the body 15 is at least partially outside the tube 3 (see FIG. 1 and arrow F3).

The first endpiece 1 consists of a disposable suction tip that can be connected to the free end of the tube 3. The body of the suction tip 1 is transparent and diminishes in thickness towards the free end through which the fluid F and the reagent 2 are sucked in. Since the first endpiece 1 is transparent, the quality and color of the fluid F sucked in can be seen immediately and may be rejected even before being allowed into the container 4.

The aforementioned detection means 20 (see FIGS. 2 to 4) comprise a bowl 17 for receiving the mixture F+2 which is discharged from the container 4 when the latter is torn and which passes through the connecting means 10 of the casing 9 located above and partly covering the bowl 17.

The bowl 17 has a filtering funnel 18 through which the mixture F+2 flowing out of the container 4 passes.

Figure 4:
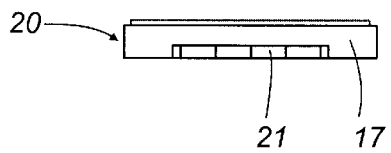
FIG. 4 is a schematic side view of a part of the detecting unit according to the present invention, in a configuration in which the result is displayed.

The bowl 17 also contains color reaction elements 21 that are activated when they come into contact with the mixture F+2 to display a result, after the filtering funnel 18 has been removed if necessary (see FIG. 4).

The container 4, the casing 9 and the detection means 20 are preferably also of the disposable type in addition to the first endpiece 1.

With a device of this type, health-care providers or their assistants can detect infectious agents, antibodies or other biological indicators in a fluid drawn from patients under treatment directly in the dental surgery using a method comprising the following steps:

collecting firstly a predetermined quantity of fluid F from the patient by suction through the first endpiece 1;

collecting secondly a predetermined quantity of reagent and/or conditioning means 2 by suction through the first endpiece 1, and simultaneously pre-mixing the reagent and/or conditioning means 2 with the fluid F (see arrows F+2 in FIG. 1);

introducing the fluid F and the reagent and/or conditioning means 2 in the container 4 at the same time as or after they have been completely mixed; and opening the container 4 to discharge the mixture F+2 thus obtained into the detecting means 20 to provide a diagnosis (see arrow F1 in FIG. 2).

Figure 3:
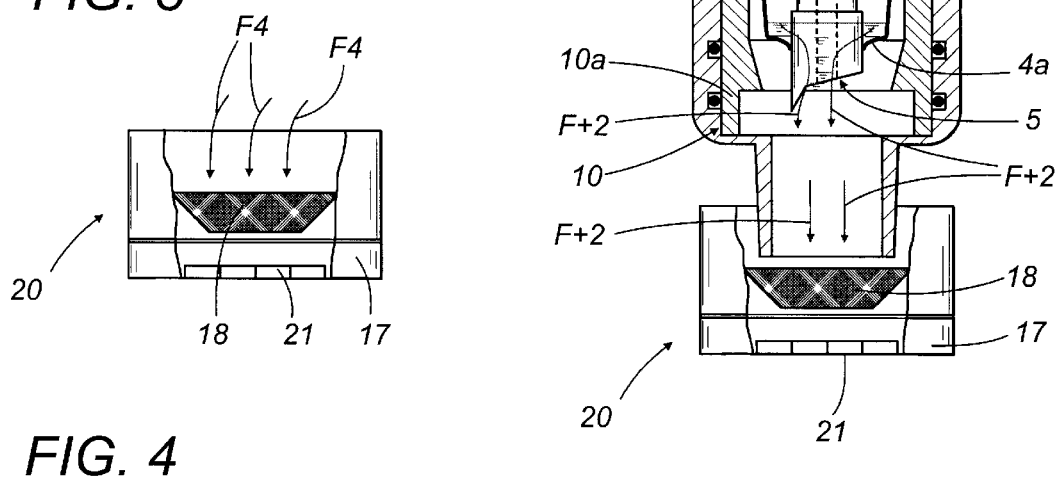
FIG. 3 is a schematic side view, with some parts cut away in order to better illustrate others, of a detecting unit that receives a fluid mixture in order to detect infectious agents in it.

Preferably, after the discharging step, the method comprises a step of adding a further quantity of reagent 2 to the mixture F+2 on the detection means 20 so as to obtain a clearly visible result (see arrows F4 in FIG. 3).

As mentioned above, the first step of collecting the fluid F may be followed by a step of visually checking the quantity and/or quality of the fluid so that it can be rejected if it is considered insufficient or unsuitable.

The device made in this way thus accomplishes the preset aims through an extremely simple kit that is easy to use and that allows different infectious agents, antibodies or other biological indicators to be detected by simply changing the type of reagent and/or the detection means.

The disposable kit consisting of first endpiece, suction tube, chamber and casing is extremely economical, practical and safe to use not only for health-care providers and their assistants but also for the patients undergoing treatment.

The invention described can be subject to numerous modifications and variations without thereby departing from the scope of the inventive concept. Moreover, all the details of the invention may be substituted by technically equivalent elements.

What is claimed:

1. A device for detecting infectious agents, antibodies or other biological indicators in a biological fluid drawn from a patient undergoing a treatment in a dental surgery, the device comprising:

a first endpiece for collecting a sample of a fluid from a patient and mixing a predetermined quantity of it with means for reacting with and/or conditioning the biological agents;

a suction tube forming an extension of the first endpiece and designed to thoroughly mix the fluid with the reagent and/or conditioning means and to introduce the mixture in a container that receives the mixture consisting of the fluid and the reagent and/or conditioning means; and means for opening the container designed to permit a controlled discharge of the mixture into corresponding detecting means to obtain a result.

2. The device according to claim 1, wherein the opening means are made on the suction tube.

3. The device according to claim 1, further comprising a dental unit having at least one suction conduit extending from an outer operative end including a second endpiece designed to accommodate a suction cannula, to an end that leads into a tank or drain, wherein the suction tube and the container are housed in a casing equipped with means for connecting to the operative end of the suction conduit in such a way that the suction conduit is used to suck in and mix fluid and reagent.

4. The device according to claim 3, wherein the casing comprises a hollow, cylindrical body equipped at one end with a cylindrical fitting, which constitutes said connecting means and which can be detachably fitted to the operative end of the suction conduit, and at the other end with an element for supporting the suction tube protruding from the casing.

5. The device according to claim 1, wherein the means for opening the container comprises a sharp taper at one end of the tube designed to tear the bottom of the container when the tube is moved axially, thus allowing the mixture to be discharged.

6. The device according to claim 1, wherein the tube comprises manual control means for turning on the suction so that the fluid and the reagent are sucked into the first endpiece separately and in a controlled manner.

7. The device according to claim 6, wherein the manual control means for turning on the controlled suction of the fluid and reagent consist of a pushbutton connected to, and able to slide radially through, the tube and equipped with a body having a conduit running transversally through the body itself; the conduit having two openings which are axially offset relative to each other so as to enable the body to be moved between a position where it is completely inside the tube so that the fluid and the reagent can be sucked into the first endpiece, and position where the suction is switched off.

8. The device according to claim 1, wherein the first endpiece consists of a disposable suction tip that can be connected to the free end of the tube; the body of the suction tip being transparent and diminishing in thickness towards the free end through which the fluid and the reagent are sucked in.

9. The device according to claim 1, further comprising detection means comprising a bowl that receives the mixture which is discharged from the container and passed through the connecting means of the casing when the container is torn.

10. The device according to claim 9, wherein the bowl has a filtering funnel through which the mixture discharged from the container passes.

11. The device according to claim 9, wherein the bowl contains color reaction elements that are activated when they come into contact with the mixture.

12. The device according to claim 1, wherein said device comprises a casing and wherein the suction tube is axially movable along the casing and is equipped with limit stop means for allowing a bottom of the container to be torn and for keeping the suction tube in a position in which the mixture can be discharged.

13. The device according to claim 1, wherein the container is of the disposable type.

14. The device according to claim 1, wherein the tube is of the disposable type.

15. The device according to claim 1, wherein the casing is of the disposable type.

16. The device according to claim 2, wherein the casing comprises a hollow, cylindrical body equipped at one end with a cylindrical fitting, which constitutes the above mentioned connecting means and which can be detachably fitted to the operative end of the suction and discharge conduit and at the other end with an element for supporting the suction tube protruding from the casing.

17. A device for detecting infectious agents in connection with a dental procedure, said device comprising:
- a first endpiece for collecting a sample of fluid from a patient and at least one of a reagent and a conditioner, said first end piece comprising a suction tube;
- a container in fluid communication with the suction tube to receive said sample and said at least one of said reagent and conditioner mixed with said sample;
- means for selectively piercing the container; and,
- detecting means for detecting infectious agents, said detecting means in communication with said container when said container is pierced by said means for selectively piercing the container.

* * * * *